United States Patent
Hopkins

(12) 
(10) Patent No.: US 7,504,249 B2
(45) Date of Patent: Mar. 17, 2009

(54) **BIOCONTROL OF DISEASE CAUSED BY VIRULENT STRAINS OF *XYLELLA FASTIDIOSA* BY CROSS PROTECTION WITH BENIGN STRAINS OF *XYLELLA FASTIDIOSA***

(75) Inventor: Don L. Hopkins, Citra, FL (US)

(73) Assignee: University of Florida Research Foundation, Gainesville, FL (US)

( * ) Notice: Subject to any disclaimer, the term of this patent is extended or adjusted under 35 U.S.C. 154(b) by 888 days.

(21) Appl. No.: 10/933,841

(22) Filed: Sep. 3, 2004

(65) Prior Publication Data

US 2005/0053584 A1 Mar. 10, 2005

Related U.S. Application Data

(60) Provisional application No. 60/500,848, filed on Sep. 5, 2003.

(51) Int. Cl.
*C12N 1/20* (2006.01)
*C12N 1/00* (2006.01)
*A01N 63/00* (2006.01)

(52) U.S. Cl. ............... 435/252.1; 435/822; 504/117
(58) Field of Classification Search ............... None
See application file for complete search history.

(56) References Cited

U.S. PATENT DOCUMENTS 5,229,292 A * 7/1993 Stock et al. ............... 424/93.2

FOREIGN PATENT DOCUMENTS

WO   WO 00/76941   12/2000

OTHER PUBLICATIONS

Hoddle M.S. "Applied Biological Control". In: The Buzz. UC Riverside, Department of Entomology Newsletter. 2002, pp. 1-4.*
Hopkins, D.L. (1992) "Induced resistance to Pierce's disease of grapevine by weakly virulent strains of *Xyella fastidiosa*" In: *Plant Pathogenic Bacteria*, Versailles, France, Jun. 9-12, Ed. INRA, Paris 1994 (Les Colloques, n°66) pp. 951-956.
Hopkins. D.S. and R.L. Wichman (2001) "Pathogenic and molecular relationships among strains of *Xylella fastidiosa* from grapevine and American elder" In: Taxonomy and Diversity, Ed. S.H. De Boer, Kluwer Academic Publishers, Netherlands, pp. 161-164.

* cited by examiner

*Primary Examiner*—Vera Afremova
(74) *Attorney, Agent, or Firm*—Saliwanchik, Lloyd & Saliwanchik

(57) ABSTRACT

This invention involves the introduction of "benign" strains of *X. fastidiosa* into desirable plants that are normally susceptible to Pierce's disease (PD). In certain embodiments, plants are injected with the benign biocontrol strain prior to transplanting into the vineyard, or immediately after transplanting. Such inoculated plants are, typically, resistant to PD for at least about 3-4 years. Various embodiments of the subject invention also provide for "booster injections" every 3-4 years. The subject invention also provides "benign" bacterial strains suitable for control of PD and compositions comprising the aforementioned "benign" bacterial strains.

12 Claims, No Drawings

BIOCONTROL OF DISEASE CAUSED BY VIRULENT STRAINS OF *XYLELLA FASTIDIOSA* BY CROSS PROTECTION WITH BENIGN STRAINS OF *XYLELLA FASTIDIOSA*

CROSS REFERENCE TO RELATED APPLICATIONS

This application claims the benefit of U.S. Provisional Application 60/500,848, filed Sep. 5, 2003, which is hereby incorporated by reference in its entirety.

Pierce's disease (PD) is a lethal disease of grapevines that is caused by *Xylella fastidiosa* and is spread by certain leafhoppers known as sharpshooters. Pierce's disease is currently restricted to the Americas and is named after N. B. Pierce. The disease was first reported in California in 1892.

BACKGROUND OF THE INVENTION

In the past, PD epidemics erupted sporadically in various locations and years to cause severe losses in vineyards. PD is especially damaging in the southeastern USA where it is endemic and is the primary factor limiting the development of a grape industry based on the high-quality European grapes (*Vitis vinifera*). PD also is a limiting factor in the production of European grapes in parts of Mexico, Central America, and southwestern USA. Losses to PD may require major replanting where infestations are wide-spread Strains of *Xylella fastidiosa* cause economic losses in many other agriculturally important plants, including grapevine, peach, plum, coffee, and citrus. They also cause leaf scorch and declines in many urban shade trees and shrubs, such as elm, oak, oleander, maple, and sycamore. Many strains of *Xylella fastidiosa* have been discovered, and almost all of these cause leaf scorching of woody perennials such as American elm, maple, mulberry, or plum. *Xylella fastidiosa* infection of some plants results in slowing of growth or stunting. Some strains of *X. fastidiosa* have very wide host ranges.

*Xylella fastidiosa* colonizes the xylem (water conducting elements of plants) and is introduced into plants by insects with piercing/sucking mouthparts that feed on xylem sap. These insects transmit the bacteria from diseased to healthy plants. Plants develop symptoms when the xylem is blocked, thus reducing the flow of water to leaves.

The first evidence of PD infection usually is a drying or "scorching" of leaves. Typically, leaves become slightly yellowed along the margins before drying. In some instances, the outer leaf may dry suddenly while still green. Typically, the leaf dries progressively over a period of days to weeks, leaving a series of concentric zones of discolored and dead tissue.

Currently, the only feasible control for diseases caused by *X. fastidiosa* is resistance. Virulence to grape of *X. fastidiosa* strains originally obtained from grapevines with PD varies from avirulent to highly virulent. Weakly virulent strains multiply and move systemically, but more slowly in the plant, producing only minor symptoms. Restriction endonuclease fingerprinting of *X. fastidiosa* with NotI and SfiI showed a high degree of similarity between the strains from American elder and grapevine.

BRIEF SUMMARY OF THE INVENTION

This invention comprises the introduction of "benign" strains of *X. fastidiosa* into desirable plants that are normally susceptible to Pierce's disease. In certain embodiments, plants are injected with the benign biocontrol strain prior to transplanting, or immediately after transplanting. Such inoculated plants are, typically, resistant to PD for at least about 3-4 years. Various embodiments of the subject invention also provide for "booster injections" every 3-4 years. The subject invention also provides "benign" bacterial strains suitable for control of PD and compositions comprising the aforementioned "benign" bacterial strains.

DETAILED DESCRIPTION OF THE INVENTION

One aspect of the subject invention provides "benign" bacterial strains, and compositions thereof comprising a physiologically acceptable carrier, suitable for the biocontrol of PD in desirable plants. In preferred embodiments, *X. fastidiosa* strains isolated from American elder are used for the biocontrol of PD in desirable plants. In a more preferred embodiment, the EB92-1 strain of *X. fastidiosa* is used in the practice of the subject invention. The EB92-1 strain of *X. fastidiosa* was deposited has been deposited with the American Type Culture Collection (10801 University Blvd., Manassas, Va. 20110-2209 USA) on Aug. 5, 2003 and has accession number PTA-5370. In various embodiments, the subject invention provides *X. fastidiosa* strains that have not been genetically modified (e.g., a non-transformed strain of *X. fastidiosa*) for control of PD. Additional exemplary strains for use in the methods of the subject invention include those from elderberry (such as *X. fastidiosa* EB92-2, *X. fastidiosa* EB92-5, *X. fastidiosa* EB-95-1) and isolates from other trees, such as sycamore (*X. fastidiosa* Scy86-1 for example).

The culture deposited for the purposes of this patent application, *Xylella fastidiosa* strain EB92-1 was deposited under conditions that assure that access to the culture is available during the pendency of this patent application to one determined by the Commissioner of Patents and Trademarks entitled thereto under 37C.F.R. §1.14 and 35 U.S.C. §122.*Xylella fastidiosa* strain EB92-1 was deposited with tbe American Type Culture Collection (10801 University Blvd., Manassas, Va. 20110-2209 USA) on Aug. 5, 2003 and has accession number PTA-5370. The deposit will be available as required by foreign patent laws in countries wherein counterparts of the subject application, or its progeny, are filed. However, it should be understood that the availability of a deposit does not constitute a license to practice the subject invention in derogation of patent rights granted by government action.

Further, the subject culture deposit (PTA-5370) will be stored and made available to the public in accord with the provisions of the Budapest Treaty for the deposit of biological materials, i.e., they will be stored with all the care necessary to keep them viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit should the depository be unable to furnish a sample when requested, due to the condition of a deposit. All restrictions on the availability to the public of the subject culture deposit will be irrevocably removed upon the granting of a patent disclosing it.

Compositions comprising "benign" bacterial strains (as set forth in paragraph 8) suitable for the biocontrol of PD in desirable plants can further comprise additional biocontrol agents and physiologically acceptable carriers. For example, compositions of the subject invention can further comprise one or more of the following biocontrol agents: mymarid egg parasitoids of the genus *Gonatocerus* e.g., *G. triguttatus, G. fasciatus, G. ashmeadi*; bacterial cells transformed with insecticidal toxins, such as Bt (*Bacillus thuringiensis*) toxin, or transformed *X. fastidiosa* cells. Physiologically acceptable carriers include, for example, sterile or non-sterile: water, saline, liquid or solid bacterial growth media, or buffered solutions (e.g., phosphate buffered saline or phosphate buffers).

The term "desirable plants" includes, and is not limited to, grapevine, peach, plum, coffee, citrus, urban trees, such as oak, elm, willow, hickory and ornamental shrubs typically used in home landscaping applications.

The subject invention also provides for methods of reducing the incidence of disease caused by *X. fastidiosa* (e.g., PD) in desirable plants comprising the administration of a composition comprising, consisting essentially of, of consisting of *X. fastidiosa* strains (as set forth in paragraphs 8 through 11) to the plants. *X. fastidiosa* strains can be administered to plants via mechanical means that allows for the introduction of the bacterial strains into the plant and, ultimately, into the xylem of the plant. For example, leaves can be mechanically disrupted to allow the pathogen to enter the xylem of the plant or a pin-pricking technique to introduce the pathogen into a susceptible plant. In various embodiments of the subject invention, compositions comprising *X. fastidiosa* strains can be administered as "boosters" to previously inoculated desirable plants. These "booster" administrations of such compositions can occur at any time point after the initial administration of the compositions of the subject invention (for example at a time point at least 0.5, 1, 1.5, 2, 2.5, 3, 3.5, 4, 4.5, or 5 five years after the initial administration of said compositions). In certain preferred embodiments, *X. fastidiosa* strains that have not been genetically modified (e.g., a non-transformed strain of *X. fastidiosa*) are used. The method set forth above can also be used to reduce the incidence of leaf scorch in desirable plants.

The subject invention also provides methods of producing *X. fastidiosa* resistant vineyards, orchards, or groves comprising the administration of a composition comprising, consisting essentially of, or consisting of protective ("benign") *X. fastidiosa* strains to young grapevines, seedlings, or rootstock; planting said grapevines, seedlings, or rootstock; and growing said grapevines, seedlings, rootstock to establish a vineyard, orchards, or groves. In some embodiments, a benign strain can be administered to grapevines prior to transplanting into the vineyard, or immediately after transplanting. Where plants are injected with *X. fastidiosa* prior to planting, said grapevines, seedlings, or rootstock can be maintained for a period of time under conditions that preclude infection with virulent strains of *X. fastidiosa* (e.g., for a period of at least one, two, three, four, five, six, seven, eight, or more weeks). Resistance to Pierce's disease in grapevine is effective for about 3-4 years. The method can further comprise booster injections as necessary (e.g., every 3-4 years). In certain preferred embodiments, *X. fastidiosa* strains that have not been genetically modified (e.g., a non-transformed strain of *X. fastidiosa*) are used and strains/compositions as set forth in paragraphs 8 through 11 can be used in the practice of the instant invention.

In one vineyard test, a planting of 'Cabernet Sauvignon' on 'Freedom' rootstock was established in the University of Florida vineyard at the research center in Leesburg, Fla. These plants were injected with strains of *X. fastidiosa* that were avirulent, or weakly virulent, to grapevine as soon as new cane growth was 18" to 30" long and received no additional injections with the protectant strains. Pierce's disease is endemic and severe in this vineyard and plants are infected within months of planting. After 48 months, all of the untreated vines were dead. The most effective strain (EB92-1) in reducing vine death was originally isolated from elderberry. In this treatment, there was no loss for 36 months, and only one vine had died after 48 months. Grapes were harvested from the remaining grapevines in this treatment.

The invention claimed is:

1. An isolated bacterium having all of the identifying characteristics of the EB92-1 strain of *Xylella fastidiosa* (ATCC Accession No. PTA-5370).

2. The isolated bacterium according to claim 1, wherein said bacterium is the EB92-1 strain of *X. fastidiosa* (ATCC Accession No. PTA-5370).

3. A composition comprising a physiologically acceptable carrier and an isolated bacterium having all of the identifying characteristics of the EB92-1 strain of *X. fastidiosa* (ATCC Accession No. PTA-5370).

4. The composition according to claim 3, further comprising one or more additional biocontrol agents.

5. The composition according to claim 4, wherein said biocontrol agent is mymarid egg parasitoids of the genus *Gonatocerus*; bacterial cells transformed with insecticidal toxins; or transformed *X. fastidiosa* cells.

6. A method of reducing the incidence of disease caused by *X. fastidiosa* in desirable plants comprising the administration of a composition comprising at least one *X. fastidiosa* strain having all of the identifying characteristics of EB92-1 strain of *X. fastidiosa* (ATCC Accession No. PTA-5370).

7. A method of producing *X. fastidiosa* resistant vineyards, orchards, or groves comprising the administration of a composition according to claim 3 to young grapevines, seedlings, or rootstock; planting said grapevines, seedlings, or rootstock; and growing said grapevines, seedlings, rootstock to establish a vineyard, orchards, or groves.

8. The method according to claim 7, wherein said *X. fastidiosa* strains have not been genetically modified.

9. The composition according to claim 5, wherein said biocontrol agent is mymarid egg parasitoids of the genus *Gonatocerus*.

10. The composition according to claim 5, wherein said biocontrol agent is bacterial cells transformed with insecticidal toxins.

11. The composition according to claim 5, wherein said biocontrol agent is transformed *X. fastidiosa* cells.

12. The method according to claim 7, wherein said composition further comprises one or more additional biocontrol agent.

* * * * *

UNITED STATES PATENT AND TRADEMARK OFFICE
CERTIFICATE OF CORRECTION

PATENT NO. : 7,504,249 B2  Page 1 of 1
APPLICATION NO. : 10/933841
DATED : March 17, 2009
INVENTOR(S) : Donald L. Hopkins It is certified that error appears in the above-identified patent and that said Letters Patent is hereby corrected as shown below:

Column 1,
Line 64, "*X. fastidiosa*into" should read --*X. fastidiosa* into--.

Column 2,
Line 18, "was deposited has been deposited" should read --has been deposited--.

Column 3,
Line 14, "consisting essentially of, of consisting" should read
       --consisting essentially of, or consisting--.
Line 36, "*X. fastidiosa*resistant" should read --*X. fastidiosa* resistant--.
Line 45, "*X. fastidiosa*prior" should read --*X. fastidiosa* prior--.
Line 53, "*X. fastidiosa*strains" should read --*X. fastidiosa* strains--.

Signed and Sealed this

Twenty-third Day of June, 2009

JOHN DOLL
*Acting Director of the United States Patent and Trademark Office*